United States Patent [19]

Schmerling

[11] 4,062,904

[45] Dec. 13, 1977

[54] REMOVAL OF HYDROXYL-, CARBOXY-, OR AMINO SUBSTITUENTS FROM AROMATIC COMPOUNDS USING A GROUP VI B CATALYST

[75] Inventor: Louis Schmerling, Riverside, Ill.

[73] Assignee: UOP Inc., Des Plaines, Ill.

[21] Appl. No.: 727,207

[22] Filed: Sept. 27, 1976

[51] Int. Cl.$^2$ .............................................. C07C 15/00
[52] U.S. Cl. ........................... 260/668 R; 260/621 R; 260/622 R; 260/667; 260/672 R
[58] Field of Search .................. 260/668 R, 621, 667, 260/672 R

[56] References Cited

U.S. PATENT DOCUMENTS

| | | | |
|---|---|---|---|
| 1,430,585 | 10/1922 | Ramage | 260/668 R |
| 1,963,258 | 6/1934 | Bröde et al. | 260/668 R |
| 3,182,094 | 5/1965 | Glazier et al. | 260/672 R |
| 3,707,470 | 12/1972 | Sawa | 260/668 R |

*Primary Examiner*—Veronica O'Keefe
*Attorney, Agent, or Firm*—James R. Hoatson, Jr.; Raymond H. Nelson; William H. Page, II

[57] ABSTRACT

Substituent groups which are positioned on the nuclei of aromatic compounds may be removed therefrom by treating the substituted compound with hydrogen at an elevated temperature in the presence of hydrogenation catalysts and particularly transition metal oxides and sulfides.

7 Claims, No Drawings

REMOVAL OF HYDROXYL-, CARBOXY-, OR AMINO SUBSTITUENTS FROM AROMATIC COMPOUNDS USING A GROUP VI B CATALYST

This invention relates to a process for the removal of substituents from the nuclei of aromatic compounds. More particularly, the invention is concerned with removing substituent groups from aromatic nuclei by heating the substituted aromatic compound under hydrogen pressure in the presence of certain hydrogenation catalysts of a type hereinafter set forth in greater detail.

In the chemical industry it is sometimes advantageous to convert some aromatic compounds, either mononuclear or polynuclear in configuration which possess certain substituents, to either unsubstituted aromatic compounds or to alkyl-substituted aromatic compounds. For example, some polynuclear aromatic compounds which contain various substituents such as hydroxyl, carboxyl or amino groups, may be utilized in the pharmaceutical industry. However, the preparation of these compounds may involve preparing, as intermediates thereof, certain compounds which contain unwanted substituents. Therefore, it is necessary to remove the unwanted substituents in order to enhance the activity of the desired compound. By utilizing the process of the present invention, it will be possible to remove certain substituents and therefore convert pharmacologically inactive compounds into compounds which do possess the desired activity.

It is therefore an object of this invention to provide a process for the removal of substituent groups from aromatic compounds.

More specifically the invention is concerned with a process for removing substituent groups from substituted aromatic compounds by treatment of the latter which hydrogen at an elevated temperature and pressure in the presence of certain catalysts.

In one aspect an embodiment of this invention resides in a process for the removal of substituent groups from the nuclei of a substituted aromatic compound which comprises treating said substituted aromatic compound with hydrogen in the presence of a hydrogenation catalyst at an elevated temperature and pressure, and recovering the resultant aromatic compound.

A specific embodiment of this invention is found in a process for the removal of substituent groups which comprises treating benzoic acid with hydrogen at a temperature in the range of from about 300° to about 500° C. and a pressure in the range of from about 1 to about 150 atmospheres in the presence of molybdenum trioxide and recovering the resultant benzene and toluene.

Other objects and embodiments will be found in the following further detailed description of the present invention.

As hereinbefore set forth the present invention is concerned with a process for the removal of substituent groups from the nuclei of an aromatic compound. The process is effected by treating substituted aromatic compounds which may be both mononuclear and polynuclear in configuration with hydrogen at an elevated temperature and pressure in the presence of certain hydrogenation catalysts. The preferred operating conditions under which the process of the present invention is effected will include temperatures ranging from about 300° up to about 500° C. or more and preferably in a range of from about 425° to about 500° C. In addition to the elevated temperature, superatmospheric pressures are also utilized, said pressures ranging from about 1 to about 150 atmospheres. In the preferred embodiment of the invention, the operating pressure is afforded by the hydrogen which is utilized in the process. However, it is also contemplated that the amount of pressure which is used may be a combination of a partial pressure of hydrogen and a partial pressure of a substantially inert gas such as nitrogen, helium, argon, etc.

The removal of the substituent group from the aromatic nuclei is effected in the presence of a hydrogenation catalyst and particularly a hydrogenation catalyst selected from the group consisting of transition metal oxides and transition metal sulfides. Some specific examples of these transition metal compounds which may be employed will include titanium dioxide, titanium peroxide, titanium sulfide, vanadium dioxide, vanadium trioxide, vanadium tetraoxide, vanadium pentaoxide, vanadium disulfide, vanadium trisulfide, vanadium pentasulfide, niobium monoxide, niobium dioxide, niobium pentaoxide, niobium monosulfide, niobium disulfide, tantalum dioxide, tantalum tetraoxide, tantalum pentaoxide, tantalum disulfide, chromic oxide, chromous oxide, chromous sulfide, chromic sulfide, molybdenum dioxide, molybdenum trioxide, molybdenum sesquioxide, molybdenum disulfide, molybdenum trisulfide, molybdenum tetrasulfide, tungsten dioxide, tungsten trioxide, tungsten disulfide, tungsten trisulfide, rhenium tetroxide, rhenium heptaoxide, rhenium tetrasulfide, cobalt molybdate, etc. It is to be understood that the aforementioned transition metal oxides and sulfides are only representative of the class of compounds which may be employed as hydrogenation catalysts and that the present invention is not necessarily limited thereto.

Examples of aromatic compounds which contain various substituents include those in which the substituents comprise hydroxyl groups, carboxy groups, amino groups, etc. Some specific examples of these compounds which may undergo the removal of such substituents will include phenol, pyrocatechol, resorcinol, hydroquinone, pyrogallol, hydroxyhydroquinone, phloroglucinol, benzoic acid, phthalic acid, isophthalic acid, terephthalic acid, aniline, o-phenylenediamine, m-phenylenediamine, p-phenylenediamine, o-cresol, m-cresol, p-cresol, o-ethylphenol, m-ethylphenol, p-ethylphenol, o-propylphenol, m-propylphenol, p-propylphenol, o-isopropylphenol, m-isopropylphenol, p-isopropylphenol, o-t-butylphenol, m-t-butylphenol, p-t-butylphenol, salicylic acid, o-methylbenzoic acid, m-methylbenzoic acid, p-methylbenzoic acid, o-ethylbenzoic acid, m-ethylbenzoic acid, p-ethylbenzoic acid o-propylbenzoic acid, m-propylbenzoic acid, p-propylbenzoic acid, o-isopropylbenzoic acid, m-isopropylbenzoic acid, p-isopropylbenzoic acid, o-methylaniline, m-methylaniline, p-methylaniline, o-ethylaniline, m-ethylaniline, p-ethylaniline, o-n-propylaniline, m-n-propylaniline, p-n-propylaniline, o-isopropylaniline, m-isopropylaniline, p-isopropylaniline, o-t-butylaniline, m-t-butylaniline, p-t-butylaniline, 1-hydroxynaphthalene, 2-hydroxynaphthalene, 1-naphthalenecarboxylic acid, 2-naphthalenecarboxylic acid, 1-aminonaphthalene, 2-aminonaphthalene, 1,2-dihydroxynaphthalene, 1,4-dihydroxynaphthalene, 1-hydroxy-4-naphthalenecarboxylic acid, 1-hydroxy-2-methylnaphthalene, 1-hydroxy-4-methylnaphthalene, 1-hydroxy-2-ethylnaphthalene, 1-hydroxy-4-ethylnaphthalene, 1-hydroxyanthracene, 1-anthracenecarboxylic acid, 1-aminoanthracene, 1,2-dihydroxyanthracene, 1,2- anthracenedicarboxylic acid, 9-anthracenecarboxylic acid, as well as similarly substituted phenanthrenes, fluorenes, acenaphthylenes, pyrenes, chrysenes, etc. As in the case of the transition metal oxides and sulfides, it is to be understood that the examples of aromatic compounds containing one or more substituents on the nuclei thereof are only representative of the class of compounds which may be treated according to the process of this invention and that said invention is not necessarily limited thereto.

The process of this invention may be effected in any suitable manner and may comprise either a batch or continuous type of operation. For example, when a batch type operation is employed, a quantity of the starting substituted aromatic compound may be charged to a pressure-resistant vessel such as an autoclave of the rotating or mixing type which also contains a catalyst of the type hereinbefore set forth in greater detail and, if desired, a solvent such as a liquid alkane or other hydrocarbon. The apparatus is then sealed and hydrogen is pressed in until the desired initial pressure has been attained. Following this, the apparatus is then heated to the predetermined operating temperature and maintained thereat for a period of time which may range from about 0.5 up to about 10 hours or more in duration. At the end of the residence time, heating is discontinued and the apparatus is allowed to return to room temperature. After discharge of the excess pressure, the apparatus is opened and the reaction mixture is recovered therefrom. The liquid reaction mixture is separated from the catalyst and subjected to conventional means of separation and purification including washing, drying, distillation, etc., whereby the aromatic compound which has had a substituent removed from the nucleus is separated from any unreacted starting material.

In addition to effecting the reaction in a batch type of operation, it is also possible to effect the process in a continuous manner. When such a type of operation is employed, the starting material is continuously charged to a reaction vessel which contains the catalyst and which is also maintained at the proper operating conditions of temperature and pressure. Hydrogen is pressed in through separate means and the reaction is allowed to proceed for a predetermined period of time. At the end of this time, the reactor effluent is continuously withdrawn from the reactor and subjected to separation steps similar in nature to those hereinbefore set forth whereby the end product is separated from any unreacted starting materials and passed to storage while said starting materials may be recycled to form a portion of the feed stock.

The following examples are given for purposes of illustrating the process of this invention. However, it is to be understood that said examples are merely illustrative in nature and that the present invention is not necessarily limited thereto.

EXAMPLE I

In this example 52 grams (0.43 mole) of benzoic acid was charged to the glass liner of an 850 cc rotating autoclave. In addition, the liner also contained 3 grams of molybdenum trioxide. The autoclave was sealed and hydrogen pressed thereto until an initial operating pressure of 100 atmospheres was reached. Thereafter the autoclave was heated to a temperature of 425° C. and maintained thereat for a period of 4 hours, the maximum pressure during this period reaching 200 atmospheres. At the end of the 4-hour period, heating was discontinued and the autoclave allowed to return to room temperature, the final pressure at room temperature being 62 atmospheres. The excess pressure was discharged and the autoclave was opened, following which the reaction mixture was recovered therefrom. Analysis of the product determined that there had been an almost complete conversion to benzene and toluene, there being recovered a 45 mole % yield of benzene and a 40 mole % yield of toluene.

EXAMPLE II

To the glass liner of a rotating autoclave was charged 49 grams (0.33 mole) of phthalic anhydride. In addition, the autoclave also contained 3 grams of molybdenum trioxide. The autoclave was sealed and 100 atmospheres of hydrogen was pressed into the autoclave. Thereafter the autoclave and contents thereof were heated to a temperature of 425° C. for a period of 4 hours, the maximum pressure at this temperature reaching 200 atmospheres. At the end of the 4-hour period, heating was discontinued and the autoclave allowed to return to room temperature, the final pressure at room temperature being 68 atmospheres. The excess pressure was discharged, the autoclave was opened and the reaction product was recovered therefrom. Analysis of this product determined that there had been a 50 mole % yield of toluene, a 25 mole % yield of benzene and a 10 mole % yield of xylene produced therein.

EXAMPLE III

In this example 29 grams of m-cresol and 7 grams of a catalyst consisting of a mixture of molybdenum trioxide and silica-alumina were placed in the glass liner of a rotating autoclave. The autoclave was sealed and 100 atmospheres of hydrogen was pressed thereto. The autoclave was then heated to a temperature of 425° C. and maintained thereat for a period of 6 hours, the maximum pressure during this time rising to 216 atmospheres. At the end of the 6-hour period, heating was discontinued and the autoclave was allowed to return to room temperature, the final pressure at room temperature being 78 atmospheres. The excess pressure was discharged, the autoclave was opened and the reaction mixture was recovered therefrom. Analysis of this product determined that there had been a practically complete conversion of m-cresol to toluene.

EXAMPLE IV

In a manner similar to that set forth in the above examples, 50 grams of 1-hydroxynaphthalene (that is 1-naphthol) and 4 grams of tungsten sulfide may be treated by charging 100 atmospheres of hydrogen to an autoclave containing said hydroxynaphthalene and tungsten sulfide, thereafter heating the autoclave to a temperature of about 450° C. and maintaining this temperature for a period of 6 hours. At the end of the 6-hour period, heating is discontinued, the autoclave may be allowed to return to room temperature, the excess pressure may be discharged and the autoclave opened. Analysis of the reaction product which may be recovered will show a substantial conversion of the hydroxynaphthalene to naphthalene.

I claim as my invention:

1. In a process for the removal of a hydroxyl-, carboxy- or amino- moiety from an aromatic compound substituted with said hydroxyl, carboxy or amino moiety which comprises contacting said aromatic compound with hydrogen at a temperature of from about 300° C. to about 500° C. and a pressure of from about 1 atmosphere to about 150 atmospheres and recovering the resultant aromatic compound, the improvement which comprises effecting said contacting in the presence of a catalyst consisting essentially of an oxide or sulfide of Group VIB of the Periodic Table of Elements.

2. The process as set forth in claim 1 in which said temperature is in a range of from about 450° C. to about 500° C.

3. The process as set forth in claim 1 in which said Group VIB oxide catalyst is molybdenum trioxide.

4. The process as set forth in claim 1 in which said Group VIB sulfide catalyst is tungsten sulfide.

5. The process as set forth in claim 1 in which said hydroxyl substituted aromatic compound is cresol and said aromatic compound is benzene.

6. The process as set forth in claim 1 in which said carboxy substituted aromatic compound is benzoic acid and said aromatic compound is a mixture of benzene and toluene.

7. The process as set forth in claim 1 in which said hydroxy substituted aromatic compound is 1-hydroxynaphthalene and said aromatic compound is naphthalene.

* * * * *